United States Patent
Bakkar

(10) Patent No.: US 10,281,457 B2
(45) Date of Patent: May 7, 2019

(54) RECONSTRUCTED SCALP MODEL AND PROCESS FOR SCREENING ACTIVE MOLECULES

(75) Inventor: Khalid Bakkar, Courbevoie (FR)

(73) Assignee: L'OREAL, Paris (FR)

( * ) Notice: Subject to any disclaimer, the term of this patent is extended or adjusted under 35 U.S.C. 154(b) by 507 days.

(21) Appl. No.: 14/122,539

(22) PCT Filed: May 30, 2012

(86) PCT No.: PCT/EP2012/060164
§ 371 (c)(1),
(2), (4) Date: Jan. 8, 2014

(87) PCT Pub. No.: WO2012/163974
PCT Pub. Date: Dec. 6, 2012

(65) Prior Publication Data
US 2014/0199721 A1    Jul. 17, 2014

Related U.S. Application Data

(60) Provisional application No. 61/492,383, filed on Jun. 2, 2011.

(30) Foreign Application Priority Data

May 30, 2011    (FR) ...................... 11 54684

(51) Int. Cl.
*C12N 5/071* (2010.01)
*G01N 33/50* (2006.01)

(52) U.S. Cl.
CPC ....... *G01N 33/5088* (2013.01); *C12N 5/0698* (2013.01); *G01N 33/5044* (2013.01); *C12N 2502/094* (2013.01); *C12N 2502/1323* (2013.01); *C12N 2503/06* (2013.01); *C12N 2533/54* (2013.01)

(58) Field of Classification Search
None
See application file for complete search history.

(56) References Cited

U.S. PATENT DOCUMENTS

2008/0097607 A1    4/2008  Bakkar et al.

FOREIGN PATENT DOCUMENTS

| EP | 1 878 790 | 1/2008 |
|----|-----------|--------|
| JP | 2005-525088 A | 8/2005 |
| JP | 2008-29342 A | 2/2008 |

OTHER PUBLICATIONS

Wu, J-J., et al., "Hair follicle reformation induced by dermal papilla cells from human scalp skin", Archives of Dermatological Research, vol. 298, No. 4, pp. 183-190, XP019426281, (Aug. 8, 2006).
Renner, R. et al., "Transplantation of chronic wounds with epidermal sheets derived from autologous hair follicles—the Leipzig experience", International Wound Journal, vol. 6, No. 3, pp. 226-232, XP002670157, (Jun. 2009).
Liu, F. et al., "Using human hair follicle-derived keratinocytes and melanocytes for constructing pigmented tissue-engineered skin", Skin Research and Technology, vol. 17, No. 3, pp. 373-379, XP002670158, (Feb. 21, 2011).
De Almeida, H. et al., "Human Scalp Dermal Papilla and Fibrous Sheath Cells have a different expression profile of Matrix Metalloproteinase in vitro when compared to Scalp Dermal Fibroblasts", Archives of Dermatological Research, vol. 297, No. 3, pp. 121-126, XP019341158, (Sep. 1, 2005).
International Search Report dated Jul. 4, 2012 in PCT/EP12/060164 Filed May 30, 2012.

*Primary Examiner* — Blaine Lankford
(74) *Attorney, Agent, or Firm* — Oblon, McClelland, Maier & Neustadt, L.L.P.

(57) ABSTRACT

The invention relates to a reconstructed scalp model, to the process for preparing it and to its use for evaluating the effect of cosmetic, pharmaceutical or dermatological topical products. The reconstructed scalp according to the invention may also be used for the preparation of the grafts intended for treating cutaneous scalp disorders.

10 Claims, 1 Drawing Sheet

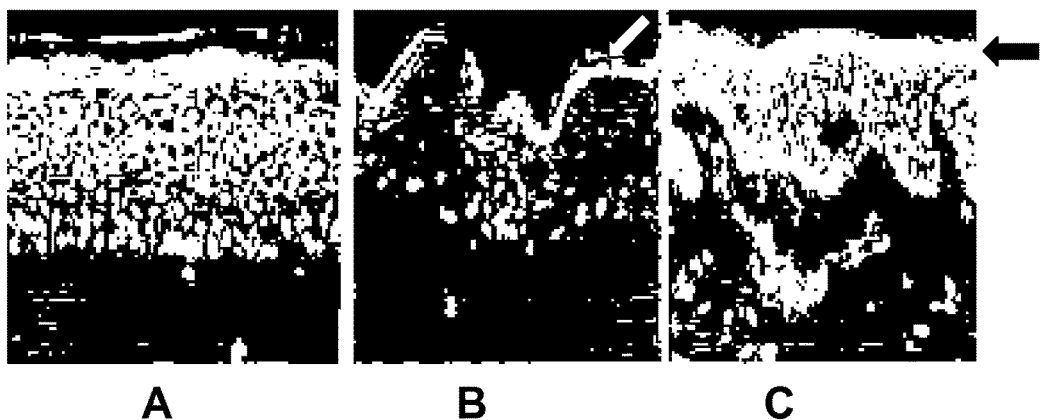
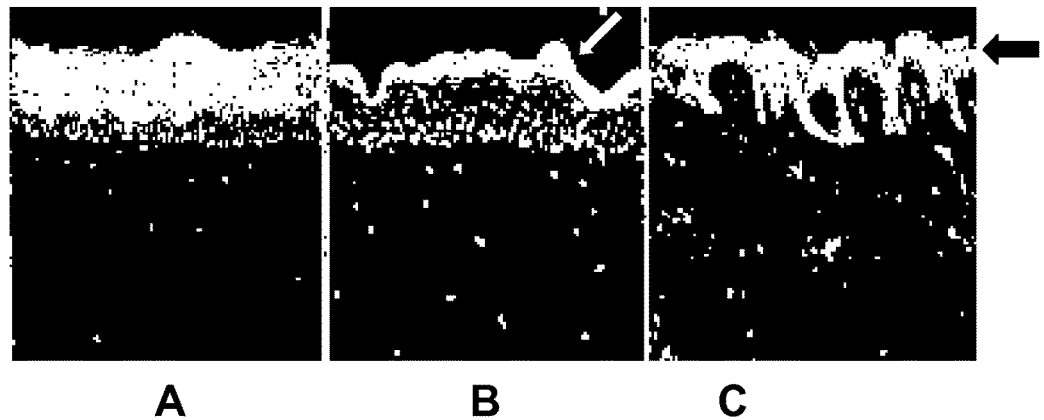

RECONSTRUCTED SCALP MODEL AND PROCESS FOR SCREENING ACTIVE MOLECULES

CROSS REFERENCE TO RELATED APPLICATIONS

The present application is a 35 U.S.C. § 371 national stage patent application of International patent application PCT/EP2012/060164, filed on May 30, 2012, published as WO/2012/163974 on Dec. 6, 2012, the text of which is incorporated by reference, and claims the benefit of the filing date of French application no. 1154684, filed on May 30, 2011, and U.S. provisional application no. 61/492,383, filed on Jun. 2, 2011, the text of each of which is also incorporated by reference.

The present invention relates to a reconstructed scalp model, to the process for preparing it and to its use for evaluating the effect of cosmetic, pharmaceutical or dermatological topical products.

The reconstructed scalp according to the invention may also be used for the preparation of grafts intended to be transplanted onto mammals, more particularly onto human patients such as sufferers of third-degree burns.

Reconstructed skin models that are more or less similar to human skin have been developed in recent years. Examples of reconstructed skin models that may be mentioned include the models described in the following documents: EP 0 285 471, EP 0 285 474, EP 0 418 035, WO 90/02796, WO 91/16010, EP 0 197 090, EP 0 020 753, FR 2 665 175, FR 2 689 904. These models firstly make it possible to perform studies necessary for better understanding of the role of the skin both in the mechanical field and in the physiological field, and secondly constitute predictive tests of the activity of cosmetic and/or pharmaceutical active agents or of the side effects of topical ingredients.

The Applicant has observed that these models are suitable for studies concerning the skin of the human body, but that they are not ideal for studies concerning a specific skin, the scalp. To the Applicant's knowledge, no reconstructed scalp model has been proposed to date.

The scalp is the part of the skin located under the head hair, i.e. over the skull. In an adult, its area may range between 650 and 700 cm$^2$. It has a conventional structure, but has several important features that distinguish it from the skin of other parts of the human body:

its epidermis is thicker, due to more rapid renewal of these cells,
its stratum corneum is thicker but is disorganised,
the activities of its hair follicles are greater due to their greater presence (about 200 to 300 follicles/cm$^2$),
the production of its sebaceous glands is intense and the activity of its sweat glands is high, which permits substantial bacterial and fungal colonization thereof.

In general, the reconstructed skin models described in the abovementioned documents are prepared from fibroblasts of the dermal papilla or of the connective sheath and/or cells taken from the outer epithelial sheath (also known as the ORS for Outer Root Sheath) on account of the ease of production of these cells. Specifically, these cells are removed when a hair is pulled out, and are capable of manufacturing an epidermis when they are placed on a support, usually a dermal equivalent, and cultured in a suitable culture medium. However, the tissue that is obtained by culturing the dermal papilla cells exhibits an expression of macromolecules (especially collagen) which does not correspond to that of an in vivo scalp. The tissue that is obtained by culturing ORS cells does not have the characteristics of a scalp either. Furthermore, the normal phenomenon of desquamation that takes place on a scalp in vivo will not be observed since, as the ORS cells have never been in contact with air, they do not desquamate. The model thus obtained therefore cannot be used for reproducing in vitro the appearance of dandruff. Finally, the sizes and morphologies of epidermides and dermides obtained by using these various cells will not be the same as those of epidermides and dermides of scalp: in the case of the scalp, the dermis is thicker and more invaginated than in the case of the skin.

The Applicant has demonstrated, surprisingly, that the culturing of interfollicular scalp cells makes it possible to develop a reconstructed scalp model that has most of the characteristics of an in vivo scalp.

One characteristic of this scalp model is the expression, in the final suprabasal layers, i.e. in the granular layers of the epidermis, of involucrin and keratin K10 (see especially FIG. 1). The cells of the granular layer are located below the stratum corneum. The granular layer (or stratum granulosum) is formed from three layers of flattened keratinocytes, with a dense oval-shaped nucleus. The tardive expression of involucrin and of keratin K10 is found on a slice of scalp obtained from a sample taken during "lifting", whereas, in a slice of reconstructed skin, the expression of these markers is observed throughout the suprabasal layers, i.e. in the cells of the layer of the malpighian mucous substance (which constitutes the stratum spinosum). This demonstrates that the scalp model according to the invention has the specificities of an in vivo scalp.

These characteristics make it possible in particular to distinguish a scalp model obtained according to the process of the invention relative to standard reconstructed skin models.

Thus, the Applicant has developed a novel process for preparing a scalp equivalent.

The Applicant isolated interfollicular scalp cells and had the idea of using them to develop a scalp equivalent.

The term "scalp equivalent", also referred to hereinbelow as a scalp model, means the assembly of a scalp epidermal equivalent laying on a scalp dermal equivalent. This is a structure produced in vitro via a technical process.

The invention thus relates to a process for preparing a scalp equivalent, comprising a step of seeding and a step of culturing interfollicular scalp keratinocytes on a dermal equivalent, the said dermal equivalent comprising collagen and interfollicular scalp fibroblasts.

The dermal equivalents may be prepared according to various processes, for instance those described in documents EP 0 418 035, WO 00/29553 or EP 0 285 471, care being taken to use the fibroblasts mentioned above.

Dermal equivalents that may be mentioned include collagen/fibroblast mixed lattices, dermis that has been de-epidermized beforehand, artificial membranes, for instance Millipore brand filters, collagen-based subcutaneous substrates, plastic or any other support that is compatible with cell viability. Preferentially, the dermal equivalent according to the invention is in the form of a collagen lattice or a collagen sponge.

The term "collagen lattice" is well known in the prior art (Bell et al. 1979, Proc. Natl. Acad. Sci. USA, Vol. 76, No. 3, pp. 1274-1278) and it denotes a known model of dermal equivalent that has been used for decades.

Preferentially, according to the invention, the lattice is prepared according to the method described by Asselineau et al., 1987 (Models in dermato., vol. III, Ed Lowe & Maibach, 1-7).

The term "collagen sponge" is also known to those skilled in the art. It denotes collagen-based biopolymers (for example: Mimedisk® sold by BASF Beauty Care).

According to the invention, the collagen may be any type of collagen of any origin. In this regard, reference will be made to the various types of collagen mentioned in the reviews by Van der Rest and Garonne, 1990, Biochem., vol. 72, 473-484 or 1991, Faseb Journal, vol. 5, 2814-2823. Thus, according to the invention, the collagen is preferably chosen from fibrillar collagens of type I, III or V.

Preferentially, according to the invention, collagen of animal origin and particularly collagen of bovine origin is used.

The collagen preferentially used according to the invention is type I collagen. Most preferentially according to the invention, bovine type I collagen is used. Needless to say, according to the invention, a mixture of different types of collagen in any proportion and/or of different origins may be used.

Preferentially, the dermal equivalent is a contracted collagen lattice and the seeding with keratinocytes is performed preferentially after 2 to 6 days, more preferentially after 3 to 5 days and even more preferentially after 3 days of contraction of the lattice. The contraction of the collagen gel is preferentially due to the action of the interfollicular scalp fibroblasts on the collagen.

The interfollicular scalp fibroblasts and/or keratinocytes are preferentially isolated, respectively, from dermis and from epidermis obtained from a scalp sample. In one preferential embodiment, the keratinocytes of the outer epithelial sheath will have been removed from this sample beforehand, for example by epilation of the hair on the said sample. The epilation of the hair on the scalp sample, for example using tweezers, will be performed so as to totally remove from the sample the keratinocytes of the outer epithelial sheath.

The interfollicular scalp keratinocytes are preferentially obtained via the following steps:
separation of the scalp dermis from the epidermis by proteolytic treatment of a scalp sample and in particular by placing a scalp sample in contact with dispase or thermolysin,
recovery of the scalp epidermis,
placing of the scalp epidermis thus obtained in contact with trypsin,
recovery of the interfollicular scalp keratinocytes and culturing of the keratinocytes thus obtained.

The keratinocytes are amplified before seeding according to the technique of Rheinwald and Green (Cell, vol. 6, 331-344,1975) by culturing on a nutrient support consisting of fibroblasts in a suitable medium known to those skilled in the art, in the presence of growth factors, especially amino acids, serum, cholera toxin, insulin, triiodothyronine and pH buffer solution. In particular, such a culture medium may especially contain at least one mitogenic growth factor for keratinocytes (for example epidermal growth factor (EGF) and/or keratinocyte growth factor (KGF), in particular KGF), insulin, hydrocortisone and optionally an antibiotic (e.g.: gentamicin or amphotericin B).

Advantageously, the said medium may also comprise serum or a pituitary extract, for example of bovine origin, epinephrine, transferrin and/or non-essential amino acids.

The fibroblasts used for this culturing will more preferentially be 3T3 fibroblasts. 3T3 fibroblasts are well known to those skilled in the art. This is a fibroblast cell line that has been known since 1962. "3T3" means "3-day transfer, inoculum of $3 \times 10^5$ cells".

The culturing of the interfollicular scalp keratinocytes is preferentially a coculture with fibroblasts (preferentially 3T3 fibroblasts) whose proliferation has been stopped beforehand, preferentially by having irradiated them beforehand (for example with UV) or by having treated them beforehand with mitomycin. Mitomycin (in particular mitomycin C) blocks the proliferation of these cells without, however, preventing them from producing the nutrient substances that are useful for keratinocyte proliferation.

According to another embodiment, the keratinocytes are amplified before seeding by culturing them on a culture medium that has been treated or supplemented with fibronectin (for example a culture box "coated with fibronectin") or with collagen (for example a culture box "coated with type I collagen") or on a rich culture medium such as the Epilife® medium (Gibco).

Dispase (also known as neutral protease) is an enzyme belonging to the protease family, which has the capacity of cleaving fibronectin and type I and IV collagens.

The interfollicular scalp keratinocytes are preferentially obtained via the following steps:
separation of the scalp dermis from the epidermis by proteolytic treatment of a scalp sample and especially by placing a scalp sample in contact with dispase or thermolysin,
recovery of the scalp dermis,
placing of the scalp dermis thus obtained in contact with collagenase and/or trypsin,
recovery of the interfollicular scalp fibroblasts and culturing of the fibroblasts thus obtained.

It is clearly understood that the enzymes mentioned above are used at concentrations, known to those skilled in the art, which enable them to have the desired effects. Preferentially, it is dispase that will be used to separate the scalp dermis from the epidermis. Trypsin (Gibco) will make it possible to obtain a suspension of interfollicular scalp keratinocytes from a scalp epidermis. Collagenase (Boehringer) and/or trypsin will make it possible to obtain a suspension of interfollicular scalp fibroblasts from a scalp dermis.

The recovery of the interfollicular scalp keratinocytes or fibroblasts is preferentially performed by filtration of the suspension obtained via the action of trypsin or collagenase, followed by centrifugation, under the conditions known to those skilled in the art, and resuspension of the centrifugation pellet.

More particularly, the process according to the invention includes:
a—seeding with the interfollicular scalp keratinocytes of a collagen lattice lying on a support immersed in a culture medium;
b—multiplication of the interfollicular scalp keratinocytes at the surface of the said collagen lattice;
c—raising of the said support such that the culture medium does not cover the upper face of the epidermal equivalent during production.

In particular, the support may be a support grille.

The dermal equivalent according to the invention is obtained in particular by seeding a culture medium with interfollicular scalp fibroblasts, followed by the addition of collagen.

The process according to the invention may comprise the following culture steps:
a) contractile cells harvested, for example, from monolayer cultures produced on a nutrient medium seeded with animal or human tissue fragments with
b) a nutrient medium supplemented with components of the dermal extracellular matrix, in particular with collagen, the said mixture forming a gel which contracts, expelling the nutrient medium to form the dermal equivalent and in particular the contracted collagen lattice.

Interfollicular scalp fibroblasts obtained from healthy human donors and harvested from monolayer cultures, by controlled trypsinization or by using collagenase, will be used as contractile cell.

The implementation of the preparation process according to the invention consists in seeding the dermal equivalent—or dermal substrate—with interfollicular scalp keratinocytes.

Conditions that enable multiplication of the keratinocytes at the surface of said substrate are maintained, the development of this interfollicular scalp keratinocyte culture being promoted by the use of at least one minimum nutrient medium, preferably a 3F medium as described in Example 1, in contact with the said keratinocytes.

Advantageously, after seeding the keratinocytes on the substrate, the implanted substrate is maintained, preferably for between 5 and 7 days, by immersion in this nutrient medium which covers the keratinocytes.

Next, the dermal equivalent is placed in contact with the air. To do this, it is placed on a support grille that is raised relative to the base of the receptacle, and the level of the nutrient medium is adjusted, so that the support grille is just covered but that the nutrient medium does not cover the upper face of the skin equivalent during production.

According to the process of the invention, the contracted dermal equivalent seeded with the interfollicular scalp keratinocytes is thus preferentially cultured for 5 to 7 days by immersion in a culture medium followed by emersion for 5 to 7 days on a suitable support.

The scalp equivalent according to the invention thus constituted is well differentiated and well organized. It is also globally homogeneous.

According to one variant of the process according to the invention, it is possible to obtain a scalp equivalent comprising hair by implanting, into the said dermal scalp equivalent (in particular into the collagen lattice), which has contracted or which is in the course of contraction, hair fibroblasts chosen from fibroblasts of the dermal papilla and/or fibroblasts of the connective sheath, and/or whole dermal papillae and/or connective sheaths and/or fractions of connective sheaths. This implementation may take place, for example, using a syringe. These hair fibroblasts, the whole dermal papillae, the connective sheaths and/or the fractions of connective sheaths will be added after the interfollicular fibroblasts have begun their action on the collagen. Their addition therefore does not take place at the same time as the interfollicular scalp fibroblasts. The hair fibroblasts will preferentially be added in an amount of 1000 to 10 000 cells, i.e. a proportion of approximately 1 to 10 hair fibroblasts per 100 interfollicular scalp fibroblasts.

By implanting the hair fibroblasts such as the papilla fibroblasts or the fibroblasts of the connective sheath or of the whole papilla or of the connective sheath or fractions of the connective sheath into the dermal equivalent, the keratinocytes will reproduce the morphogenesis of the body or head hair (hair stalk) (Reynolds A. J., Lawrence C. M., Jahoda C. A., Human hair follicle germinative epidermal cell culture. J. Invest. Dermatol. 1993 Oct.;101 (4): 634-8).

Another subject of the invention is a scalp equivalent that may be obtained via the process according to the invention.

This scalp equivalent exhibits expression of involucrin and/or of keratin K10 in its granular layers, which is expression comparable to that of an in vivo scalp. The term "comparable expression" means an expression of the genes coding for these proteins which takes place in the cells located at the same place as in the in vivo tissue and/or at the same intensity.

Given that the scalp equivalent has the characteristics of an in vivo scalp, it may be grafted in the same way and with the same success as grafts taken from the nape or the occipital region of the individual to be treated. Autograft techniques are described, for example, by Bouhanna et al. (Dermatol. Surg. ; Nov. 2003, 29(11), 1130-4). After a graft, the scalp equivalent according to the invention thus has the capacity of appropriately replacing the original scalp part.

The scalp equivalent will also find applications for the preparation of grafts intended for treating a cutaneous scalp disorder such as a burn, a cicatrization defect or canities, and thus intended to be transplanted onto mammals and more particularly onto human patients such as sufferers of third-degree burns. A graft is defined as being part of a tissue intended for grafting.

Thus, another subject of the invention concerns a scalp equivalent as defined previously, for its use for treating or in the treatment of one of the cutaneous scalp disorders mentioned above. This scalp equivalent or graft will have characteristics in terms of expression of involucrin and of keratin K10 comparable to those of an in vivo scalp (i.e. expression in the final granular layers of the epidermis of involucrin and of keratin K10). The invention thus also relates to the use of a scalp equivalent as described previously, for the manufacture of a graft for treating one of these cutaneous scalp disorders.

Irrespective of the process variant adopted for its preparation, the scalp equivalent that is obtained is a three-dimensional model that is useful as an alternative test for any test that would require animal experimentation, for example studies on the release of active agents, their cutaneous penetration and/or their absorption and/or their bioavailability, or studies on the tolerance, compatibility or efficacy of active agents and/or of cosmetic, pharmaceutical or dermatological ingredients.

Thus, another subject of the invention is the use of a scalp equivalent as described previously, for testing the cutaneous penetration and/or absorption and/or bioavailability and/or efficacy of compounds on the scalp and/or for testing the tolerance and/or compatibility of compounds with respect to the scalp.

This use thus makes it possible to see whether a compound penetrates into the various layers of the scalp, or whether it does indeed have the desired effect.

This scalp equivalent is especially useful for the identification of a compound that is a hair growth modulator and/or of molecules that act on the quality and homeostasis of the scalp and especially on the desquamation of the scalp, the treatment of dandruff or of a sensitive scalp.

It may, furthermore, enable the search for biomarkers linked with the normal or pathological status of the scalp. An additional advantage lies in the possibility of studying the implementation of hair follicles, sweat glands or sebaceous glands in order to get even closer to an in vivo scalp.

This model is necessary in order to induce the formation of the hair by injection of stem cells.

The reconstructed scalp model according to the invention may make it possible to quantify the activity of molecules that are capable of inducing the formation of hair from stem cells (for example from bulb cells).

The scalp equivalents comprising hair follicles will make it possible especially to perform body or head hair growth kinetics and thus enable any study requiring numerous live hairs that are as complete as possible in an in vivo context, such as the study of the hair cycle and of the factors capable of influencing this cycle, up to the study of active agents that promote hair growth, active agents for combating hair loss or active agents that slow down hair growth.

The product screening processes for identifying novel active agents include a step (a) of placing the said test product in contact with a scalp equivalent according to the invention and then a step (b) of analysing the effect of the said product on at least one parameter of the scalp equivalent and a step (c) of selecting the product that modifies the said parameter.

Preferably, to perform step (a), the test product is applied topically, for example formulated in standard topical formulations or else introduced into the culture medium.

The parameter of the scalp equivalent is preferentially chosen from the expression, the production and/or the activity of markers chosen beforehand in the scalp equivalent and/or the desquamation of the scalp equivalent.

Step (b) may be performed, in particular, via analysis of the expression, production and/or activity of markers associated with the quality and/or homeostasis of the scalp, for instance epidermal and/or dermal markers such as structural proteins, especially epidermal differentiation proteins and macromolecular proteins of the dermal matrix. Examples of structural proteins that may be mentioned are hair keratins.

These markers associated with the quality and/or homeostasis of the scalp may be representative of the desquamation of the scalp, of a dandruff condition or of a sensitive scalp.

When the scalp model according to the invention comprises hair fibroblasts such as papilla fibroblasts or fibroblasts of the connective sheath or of the whole papilla or of the connective sheath or fractions of the connective sheath that have been implanted as described above into the dermal equivalent, the screening tests may also be intended to identify products capable of inducing growth of the hair stalk.

To do this, step (b) of the screening process will analyse the effect on the growth of the hair stalk.

When the scalp model according to the invention comprises cells of the immune system, such as Langerhans cells, the screening tests may also be intended to identify products that are capable of inducing irritation or allergic reactions.

To do this, step (b) of the screening process will analyse the effect of the product on at least one of the parameters preferentially chosen from:
the cytotoxicity;
the release of inflammation mediators;
cell damage revealed by histology or by the release of lactate dehydrogenase (a marker of keratinocyte membrane integrity) (Roguet et al., J. Tox. In vitro 6:303 (1992) and Ponec M in In Vitro Toxicology. Eds Rougier, Maibach and Golberg p. 107, 1994);
modification of the synthesis and composition of the skin lipids, particularly the ceramides and phospholipids (JID 86, 598 (1986));
the stratification of epithelial cells as a marker of their differentiation (M. Prunieras and R. Roguet *Toxicologie cellulaire in vitro methodes et applications*, Eds M. Adolphe, A. Guillouzo and F. Marano published by INSERM 1995 pp. 191-236) (Duffy P. A., Flint O. P.: *In vitro dermal irritancy test*. In C. K. Atterwill and C. E. Steele (Eds): *In vitro methods in Toxicology*, Cambridge Univ. Press Cambridge 1987, pp. 279-297) (Use of skin cell culture for in vitro assessment of corrosion and cutaneous irritancy, Roguet, Cell Biology and Toxicology, 1999:15, 63-75).

Step (b) of analysing the effect of the product will preferentially be a comparison of at least one parameter measured on the scalp equivalent placed in contact with the test product with that or those measured on a control scalp equivalent cultured under the same conditions but which has not received the test product.

Step (c) of selecting the product that modifies the parameter of the scalp equivalent will be performed as a function of a criterion determined in advance.

The modification of this parameter may be a stimulation, a decrease or a total or partial inhibition of the expression, production and/or activity of the said markers and/or of the growth of the hair stalk and/or of the desquamation of the scalp equivalent.

The criterion for selecting the said product will be, for example, such that this product has a stimulating or inhibiting effect on the measured parameter.

The scalp equivalent according to the invention may also be used in automated screening processes for cosmetic, pharmaceutical or dermatological compounds to identify novel active agents.

FIG. 1 illustrates the invention more clearly without, however, limiting its scope.

In this figure, the photographs show slices of reconstructed skin (skin equivalent) (A), of scalp equivalent according to the invention (B) and of a scalp sample (C) after immunolabelling using anti-involucrin antibody (I) and anti-K10 antibody (II).

The examples given below are presented as non-limiting illustrations of the invention.

EXAMPLE 1

Preparation of a Scalp Model

Interfollicular scalp keratinocytes and fibroblasts are isolated from scalp samples collected during a face-lift (and thus obtained from relatively mature women) or from scalp samples obtained from relatively young men.

To isolate these scalp cells, a hair epilation is performed so as to remove the keratinocytes of the outer epithelial sheath, and the dermis is then separated from the epidermis in order to extract the two target cell populations, namely the interfollicular fibroblasts and keratinocytes.

Experimental Protocol:

Unless otherwise indicated, all the media and buffers used in the examples are described in Bell et al. 1979 (P.N.A.S. USA, 76, 1274-1278), Asselineau and Prunieras, 1984, (British J. of Derm., 111, 219-222) or Asselineau et al., 1987, (Models in dermato., vol. III, Ed. Lowe and Maibach, 1-7).

The medium MEM+10% FCS+3F (known as 3F medium) has the following composition:

| Reagent | Brand | Volume |
| --- | --- | --- |
| MEM | Biochrom KG | 500 ml |
| L-Glutamine 200 mM | Gibco | 5 ml |
| Sodium pyruvate 100 mM | Biochrom KG | 5 ml |
| NEA | Biochrom KG | 5 ml |
| FCS | Biochrom KG | 50 ml |
| Penicillin-streptomycin | Biochrom KG | 1 ml |
| Antibiotic-antimycotic | Gibco | 0.5 ml |
| EGF 10 µg/ml | TEBU | 0.5 ml |
| Cholera toxin $10^{-5}$ M | Sigma | 5 µl |
| Hydrocortisone 0.5 mg/ml | Sigma | 0.4 ml |

Place the pieces of "Top" part in a culture dish of diameter 100 mm containing 30-40 ml of dispase (Roche) and store overnight (about 15 hours) at 4° C. or store for 1 hour 30 minutes at 37° C. in a dry incubator, care being taken to cut small pieces.

1. Preparation of the Primary Culture of Normal Human Keratinocytes Remove the samples from the dispase bath and place them in a culture dish (diameter 100 mm) containing 10 ml of trypsin-EDTA (0.05%-0.02%).

Perform the separation of the dermis from the epidermis using curved tweezers and gently scrape the surface of the dermis with the back of the tweezers so as to recover the basal keratinocytes.

Place the epidermis in a conical tube (50 ml) with the 10 ml of trypsin-EDTA from the dish.

Rinse the dish with 5 ml of trypsin-EDTA.

Filter through sterile gauze.

Neutralize with 20 ml of pure foetal calf serum (FCS).

Place the suspension in a 50 ml conical tube.

Centrifuge the cell suspension for 10 minutes at 1200 rpm.

Remove the supernatant, take up the pellet with MEM 10% FCS+7F (this medium comprises the same compounds as the 3F medium and four additional compounds: adenine, transferrin, T3, insulin).

Count the viable cells.

Seed the culture dishes with 10 000 live cells/cm$^2$.

24 hours later, perform a standard coculture by adding the 3T3 (12 000 cells/cm$^2$) treated with mitomycin C (Ametycine®) without changing the medium.

2. Protocol for Isolating the Dermal Cells:

a) Prepare a solution comprising 0.1% glucose, 0.8% NaCl and 0.04% KCl.

Add collagenase to 0.1% (Worthington).

Filter the solution with a Millipore or Nalgene 0.22 μm filter.

b) Place the dermis in the form of small pieces with a side length of about 2 mm, 20 ml of the collagenase solution and a sterile bar in a 50 ml beaker.

Stir at 37° C. under 5% $CO_2$ for 1 hour 30 minutes.

Filter the suspension obtained through a double thickness of sterile gauze.

Centrifuge the filtered suspension under the usual conditions for cell centrifugation.

c) Resuspend the pellet in fresh culture medium, count the cells and seed the dishes.

3. Preparation of the Lattices:

If the experiment to be performed comprises more than 25 lattices, all the above volumes must be doubled.

MEM 1.76X
17.6 ml of MEM 10 ×
5.1 ml of $NaHCO_3$ 7.5%
0.88 ml of L-Glutamine (1.76 mM)
0.88 ml of sodium pyruvate (0.88 mM)
0.88 ml of non-essential amino acids 0.88 X (Ref.: K 0293—Supplier: Biochrom KG)
0.088 ml of penicillin streptomycin 8.8 U/8.8 μg/ml (0.088%) (Ref.: A2212—Supplier: Biochrom KG)
0.044 ml of antimycotic antibiotic 0.04 X (0.04%)
75 ml of sterile ultrapure water MEM HEPES 10% FCS
50 ml of MEM 25 mM HEPES
0.5 ml of L-Glutamine (2 mM)
0.5 ml of sodium pyruvate (1 mM)
0.5 ml of non-essential amino acids 1 X
0.1 ml of penicillin streptomycin 20 U/20 μg/ml (0.2%)
0.05 ml of antimycotic antibiotic 0.1 X (0.1%)
5 ml of FCS 10%.

NaOH 0.1N
10 ml NaOH 1N
90 ml of sterile ultrapure water

This solution is passed through a Millipore filter with a GV Durapore 0.22 μm membrane.

Acetic acid 1/1000
0.5 ml of 100% glacial acetic acid
499.5 ml of sterile ultrapure water Using the media thus prepared:

Prepare in a sterile conical flask 5 ml of the following solution:
3.22 ml of MEM 1.76 X
0.63 ml of FCS
0.35 ml of NaOH 0.1 N
0.6 ml of acetic acid 1/1000
0.2 ml of MEM HEPES 10% FCS.

Add 0.5 ml of cell suspension of interfollicular scalp fibroblasts to this solution.

Next, add slowly the necessary volume of cold collagen (2.1 ml if this collagen is Gattefossé or Symatèse collagen or 1.5 ml if it is Coletica collagen).

Shake the conical flask vigorously until homogenized (the fuchsia-pink solution turns salmon coloured).

Empty the contents of the conical flask into a 60 mm FalconØ bacteria dish.

Place the dish in the oven (37° C.-5% $CO_2$) for about 1 hour 30 minutes-2 hours.

When the gel has set and the medium expelled, check the start of contraction.

In the afternoon, shake the lattices regularly so that they do not stick together again.

Leave the contraction to proceed for 3 days.

4. Culture-seeding with Keratinocytes

The seeding with keratinocytes is performed after 3 days of contraction of the lattices.

a) Preparation of the Adhesive

Prepare 0.7 ml of the following solution, given to bond two lattices:
0.46 ml of MEM 1.76 X
0.09 ml of FCS
0.05 ml of NaOH 0.1 N
0.1 ml of MEM HEPES 10% FCS.

Add to this tube 0.3 ml of dialysed collagen. The final volume is thus 1 ml.

Comments:

The above volumes are given for the bonding of two lattices.

For several lattices, prepare a global solution corresponding to n+1 samples to be bonded in a conical flask.

Dispense, by tube, 0.7 ml of this solution using a multipipette.

Next, add 0.3 ml per tube of collagen.

Work the lattices two by two.

b) Bonding of the Lattices

Take a 6 ml tube filled with adhesive solution.

Stir with a vortex mixer.

Take up the solution by pipette and place in two Corning culture dishes a drop of about 0.45 ml of this solution into the middle of each dish.

Take up a lattice using curved tweezers and a cell lifter.

Place the lattice in the lid of its original dish in order to remove the surplus medium.

Take up the lattice and place it on the drop of adhesive.

Spread uniformly by rotating the dish so that the adhesive is distributed around the lattice.

Place the dishes in an oven (37° C.-5% $CO_2$) for 20-30 minutes to allow the adhesive to set.

c) Seeding with Keratinocytes
   Thaw the cells as quickly as possible by stirring the vial in a water bath at 37° C., if these cells were frozen.
   Transfer the contents of the vial into a 50 ml Falcon culture tube containing 35 ml of MEM 10% FCS+3F medium.
   Centrifuge for 5 minutes at 1000 rpm.
   Remove the supernatant.
   Take up the centrifugation pellet with MEM 10% FCS+3F medium to obtain a solution containing 100 000 cells/ml.
   Resuspend the cells by suction-ejection several times.
   Place a seeding ring 14 mm in diameter on the bonded lattices.
   In this ring, place 0.5 ml of cell suspension (=50 000 cells/ring 1.5 cm$^2$, i.e.
   about 33 000 cells per cm$^2$).
   Around the ring, add 5 to 7 ml of MEM 10% FCS+3F medium gently so as not to detach the lattice.
   In parallel, seed two "control rings" (dish with rings not containing lattice).
   Place the dishes in an oven at 37° C.-5% $CO_2$ for 2 hours.
   Remove the rings using curved tweezers after the 2 hours of attachment.
   Return the dishes to the oven at 37° C.-5% $CO_2$.
   Change the medium on Wednesday and Friday (5 to 7 ml of MEM 10%FCS+3F medium per dish).
Culture-Emersion of Reconstructed Skins
   After seven days of culturing in immersion, the skins are placed in emersion.
   Check, however, that the keratinocytes emerge from the lattice by observing with a microscope.
   Place an emersion grille in a Falcon bacteria dish.
   Add 7.5 ml of MEM 10% FCS+3 F while taking care to avoid the formation of bubbles.
   Cut the adhesive around the skin to be emerged using a sterile scalpel.
   Transfer the skin onto the grille with curved tweezers and a cell lifter.
   Place the dishes in the oven at 37° C.-5% $CO_2$.
   Change the medium on Wednesday and Friday (7 to 7.5 ml of MEM 10%FCS +3F medium).
   After seven days of emersion, the reconstructed scalp skins are ready to be used.

EXAMPLE 2

Comparison of the Expression of Involucrin and of Keratin K10

The expression of involucrin and of keratin K10 in the scalp equivalent obtained in Example 1 is observed after immunolabelling using mouse monoclonal antibodies directed against involucrin or against K10. This expression is also observed in a standard skin equivalent and in a scalp sample.
Preparation of the Standard Skin Equivalent and of the Scalp Sample:
   To prepare a standard dermal equivalent, 3.22 ml of MEM 1.76 X medium, 0.63 ml of foetal calf serum, 0.35 ml of 0.1 N sodium hydroxide and 0.20 ml of an MEM/HEPES medium mixture containing 10% foetal calf serum (MEM/HEPES/FCS10) are placed in a sterile Falcon tube.
   0.50 ml of MEM/HEPES/FCS10 medium containing fibroblasts obtained from human mammary surgeries prepared beforehand according to the method described by Bell et al. 1979 (P.N.A.S. USA, 76, 1274-1278), Asselineau and Prunieras, 1984, (British J. of Derm., 111, 219-222) or Asselineau et al., 1987, (Models in dermato., vol. III, Ed. Lowe & Maibach, 1-7), are then added to a concentration of $1 \times 10^6$ cells per 0.5 ml of culture medium.
   2 ml of a volume/volume mixture of collagen at a concentration of 3 mg/ml in acetic acid to 1/1000 are then added slowly, down the wall of the tube so as to observe the appearance of a whitish cloud. The whole is then mixed cautiously and placed in a Petri dish 60 mm in diameter (Falcon 60 mm type, ref. 1016). The Petri dish is then placed in an oven at 37° C. and left for about 2 hours 30 minutes. When the appearance of two phases (gel+medium) is observed, the lattice is cautiously detached from its support, and the lattice thus detached from its support is left for 4 days in the oven.
   To prepare a standard skin equivalent, the standard dermal equivalent is spread in a Corning type culture dish 60 mm in diameter on a drop of collagen "adhesive" (0.6 ml) and then maintained at 37° C. in an oven for 20-30 minutes.
   A sterile steel ring is placed on the lattice and 0.5 ml of a cell suspension of human keratinocytes obtained from mammary surgeries prepared according to Régnier et al. (Frontier of Matrix Biology, Vol. 9, 4-35, Karger, Basle 1981), at a rate of 100 000 cells/ml in MEM 10% FCS+3F medium are placed inside the ring.
   About 6 ml of medium (MEM 10% FCS+3F) are placed around the ring and the dish is placed in an oven at 37° C. for 2 hours. The ring is then removed and the dish is returned to the oven.
   After eight days, the culture is then placed at the air/liquid interface, the said liquid then consisting of the same medium as previously.
   Culturing is then continued for 1 week until a histologically satisfactory epidermal equivalent is obtained, i.e. an epidermal equivalent that has the four standard cell layers, namely the basal, suprabasal, granular and horny layers.
   The scalp sample is recovered after lifting according to the methods known to those skilled in the art.
Measurement of the Expression of Involucrin and of Keratin K10
   After freezing, the various tissues are cut into slices 5 μm thick using a cryostat.
   The slices are then rinsed twice with PBS and 25 μl of anti-involucrin antibody (Sigma - Ref.: I9018) and anti K10 antibody (Immuquest Ltd -Ref. AE20) diluted to 1/50 are placed on each slice and left for 30 minutes at room temperature (25° C.). The slices are then rinsed twice with PBS and 25 μl of FITC conjugated antibody (Rabbit anti-mouse FITC, Dako F232), are deposited on each slice and left for 30 minutes at room temperature (25° C.). The slices are rinsed twice with PBS and observed after mounting under a Leica brand fluorescence microscope, Leitz DMRB model.
   The observation shows that in the control (reconstructed skin), involucrin (FIG. 1, I) and keratin K10 (FIG. 1, II) are expressed in all the suprabasal layers of the reconstructed epidermis (FIG. 1, A), whereas they are expressed tardively, i.e. only in the granular layers, of the epidermis of the scalp equivalents (FIG. 1, B) and of the scalp samples (FIG. 1, C).
   The expression of these two markers takes place early in the reconstructed skin (A) and tardively in the reconstructed scalp model (B) and in the scalp sample (C) at the places indicated by the arrows in FIG. 1.
   These results thus make it possible to confirm that the reconstructed scalp model according to the invention is similar to the structure and functionality of an in vivo scalp.

The invention claimed is:

1. A process for preparing a scalp equivalent, the process comprising seeding and culturing interfollicular scalp keratinocytes on a dermal equivalent, wherein the dermal equivalent comprises collagen and interfollicular scalp fibroblasts, wherein the interfollicular scalp keratinocytes are obtained from a scalp sample from which keratinocytes of an outer epithelial sheath have been removed beforehand.

2. The process of claim 1, wherein the dermal equivalent is a contracted collagen lattice and the seeding with keratinocytes is performed after 2 to 5 days of contraction of the lattice.

3. The process of claim 1, wherein the interfollicular scalp fibroblasts and keratinocytes are isolated, respectively, from dermis and epidermis obtained from a scalp sample.

4. The process of claim 1, wherein the interfollicular scalp keratinocytes are obtained by:
   separating the scalp dermis from the epidermis by proteolytic treatment of the scalp sample,
   recovering the scalp epidermis,
   placing the recovered scalp epidermis in contact with trypsin,
   recovering the interfollicular scalp keratinocytes, and
   culturing the recovered keratinocytes.

5. The process of claim 4, wherein the keratinocyte culture is a coculture with fibroblasts treated beforehand with mitomycin or irradiated or a culture on a culture medium supplemented with fibronectin or with collagen.

6. The process of claim 1, wherein the interfollicular scalp fibroblasts are obtained by:
   separating the scalp dermis from the epidermis by proteolytic treatment of the scalp sample,
   recovering the scalp dermis,
   placing the recovered scalp dermis in contact with collagenase, trypsin, or both collagenase and trypsin,
   recovering the interfollicular scalp fibroblasts, and
   culturing the recovered fibroblasts.

7. The process of claim 2, wherein the contracted dermal equivalent seeded with the interfollicular scalp keratinocytes is cultured for 5 to 7 days by immersion in a culture medium followed by emersion for 5 to 7 days on a suitable support.

8. The process of claim 2, further comprising implanting hair fibroblasts selected from the group consisting of fibroblasts of the dermal papilla, fibroblasts of the connective sheath, whole dermal papillae, connective sheaths, and fractions of connective sheaths into the dermal equivalent that has contracted or that is in the course of contraction.

9. The process of claim 1, wherein the collagen is a type I fibrillar collagen, a type II fibrillar collagen or a type III fibrillar collagen.

10. The process of claim 1, wherein the collagen is a type I fibrillar collagen.

* * * * *